(12) United States Patent
Deng et al.

(10) Patent No.: US 10,139,938 B2
(45) Date of Patent: Nov. 27, 2018

(54) MOBILE TERMINAL

(71) Applicant: SHENZHEN GOODIX TECHNOLOGY CO., LTD., Shenzhen, Guangdong (CN)

(72) Inventors: Gengchun Deng, Guangdong (CN); Wei Long, Guangdong (CN)

(73) Assignee: SHENZHEN GOODIX TECHNOLOGY CO., LTD., Shenzhen, Guangdong (CN)

( * ) Notice: Subject to any disclaimer, the term of this patent is extended or adjusted under 35 U.S.C. 154(b) by 46 days.

(21) Appl. No.: 15/249,997

(22) Filed: Aug. 29, 2016

(65) Prior Publication Data
US 2016/0364036 A1 Dec. 15, 2016

Related U.S. Application Data

(63) Continuation of application No. PCT/CN2014/088291, filed on Oct. 10, 2014.

(30) Foreign Application Priority Data

Jun. 16, 2014 (CN) .......................... 2014 1 0268589

(51) Int. Cl.
*G06F 3/041* (2006.01)
*H04B 1/38* (2015.01)
(Continued)

(52) U.S. Cl.
CPC .......... *G06F 3/041* (2013.01); *A61B 5/02438* (2013.01); *A61B 5/117* (2013.01);
(Continued)

(58) Field of Classification Search
CPC ... A61B 5/117; A61B 5/1172; A61B 5/14542; A61B 5/02438; A61B 5/6898;
(Continued)

(56) References Cited

U.S. PATENT DOCUMENTS 6,088,585 A * 7/2000 Schmitt ................ G06K 9/0002
340/5.83
6,098,330 A * 8/2000 Schmitt ................ F41A 17/066
382/145
(Continued)

FOREIGN PATENT DOCUMENTS

AU 2013100571 A4 3/2013
CN 101561727 A 10/2009
(Continued)

OTHER PUBLICATIONS

State Intellectual Property Office of the P. R. C., "First Chinese Office Action for Application No. 201410268589.3", China, dated Jun. 13, 2016.
(Continued)

*Primary Examiner* — Michael J Eurice
(74) *Attorney, Agent, or Firm* — Tim Tingkang Xia, Esq.; Locke Lord LLP

(57) ABSTRACT

The present invention discloses a mobile terminal, including a touch screen, the touch screen including a touch cover plate. The touch screen further includes a sensing identification module, the touch cover plate covering the sensing identification module. In the embodiments of the present invention, the sensing identification module is integrated into a touch screen, and a full touch panel is used. In this way, the problem of sense of difference which is brought by the independently assembled sensing identification module is solved from the visual and tactile perspectives, the manufacturing procedure is simplified, production and utilization efficiencies are improved, and user's satisfaction is enhanced.

14 Claims, 5 Drawing Sheets

(51) Int. Cl.
    *H04M 1/23*     (2006.01)
    *A61B 5/024*     (2006.01)
    *A61B 5/1172*     (2016.01)
    *A61B 5/145*     (2006.01)
    *A61B 5/00*     (2006.01)
    *G06K 9/00*     (2006.01)
    *G06F 1/16*     (2006.01)
    *A61B 5/117*     (2016.01)

(52) U.S. Cl.
    CPC ........ *A61B 5/1172* (2013.01); *A61B 5/14542* (2013.01); *A61B 5/6898* (2013.01); *G06F 1/1643* (2013.01); *G06F 1/1684* (2013.01); *G06K 9/00013* (2013.01); *G06K 9/00053* (2013.01); *G06F 2203/04103* (2013.01)

(58) Field of Classification Search
    CPC ...... G06F 3/041; G06F 1/1643; G06F 1/1684; G06F 2203/04103; G06K 9/00013; G06K 9/00053; G06K 9/00
    See application file for complete search history.

(56) References Cited

U.S. PATENT DOCUMENTS

| | | | | |
|---|---|---|---|---|
| 8,717,775 | B1* | 5/2014 | Bolognia | G06K 9/00053 361/761 |
| 2003/0215116 | A1* | 11/2003 | Brandt | G06K 9/00053 382/124 |
| 2005/0069178 | A1* | 3/2005 | Nysaether | G06K 9/0002 382/124 |
| 2009/0169071 | A1 | 7/2009 | Bond et al. | |
| 2009/0309180 | A1* | 12/2009 | Yamagata | G06K 9/0002 257/435 |
| 2010/0096710 | A1* | 4/2010 | Chou | G06K 9/0002 257/414 |
| 2010/0113952 | A1* | 5/2010 | Raguin | G06K 9/0012 600/509 |
| 2010/0153764 | A1* | 6/2010 | Pratt | G06F 1/3203 713/324 |
| 2011/0001708 | A1* | 1/2011 | Sleeman | G06F 3/0416 345/173 |
| 2011/0070827 | A1* | 3/2011 | Griffin | H04B 5/02 455/41.1 |
| 2011/0215484 | A1* | 9/2011 | Bond | G06K 9/0002 257/787 |
| 2011/0309482 | A1* | 12/2011 | Salatino | G06K 9/00053 257/659 |
| 2012/0268423 | A1* | 10/2012 | Hotelling | G06F 3/0412 345/174 |
| 2013/0106603 | A1* | 5/2013 | Weast | G06F 1/163 340/539.11 |
| 2013/0120106 | A1* | 5/2013 | Cauwels | G06F 1/163 340/3.1 |
| 2013/0194071 | A1* | 8/2013 | Slogedal | G06K 9/0002 340/5.82 |
| 2013/0196596 | A1* | 8/2013 | Parekh | G06F 1/1643 455/41.1 |
| 2013/0259329 | A1* | 10/2013 | Wickboldt | H05K 1/189 382/124 |
| 2014/0133715 | A1 | 5/2014 | Ballard et al. | |
| 2014/0140588 | A1 | 5/2014 | Chou | |
| 2014/0333328 | A1* | 11/2014 | Nelson | G06F 3/044 324/663 |
| 2014/0341448 | A1* | 11/2014 | Chiu | G06K 9/0002 382/124 |
| 2014/0369573 | A1* | 12/2014 | Chiu | G06K 9/00013 382/124 |
| 2015/0103018 | A1* | 4/2015 | Kamin-Lyndgaard | G09G 5/006 345/173 |
| 2015/0242672 | A1* | 8/2015 | Benkley, III | G06K 9/0002 382/124 |
| 2016/0110025 | A1* | 4/2016 | Hossu | G06F 3/0412 382/124 |
| 2016/0335468 | A1* | 11/2016 | Long | G06K 9/0002 |
| 2016/0379036 | A1* | 12/2016 | Long | G06K 9/00013 382/124 |
| 2017/0075483 | A1* | 3/2017 | Ling | G06F 3/044 |

FOREIGN PATENT DOCUMENTS

| | | |
|---|---|---|
| CN | 203405776 U | 1/2014 |
| CN | 103793688 A | 5/2014 |
| CN | 103793691 A | 5/2014 |
| CN | 104049803 A | 9/2014 |
| GB | 2496055 A | 5/2013 |
| KR | 101368262 B1 | 2/2014 |
| WO | 2013100067 A1 | 7/2013 |

OTHER PUBLICATIONS

State Intellectual Property Office of the P.R. China (ISR/CN), "International Search Report for PCT/CN2014/088291", China, dated Feb. 27, 2015.

European Patent Office, "Extended European Search Report for EP Application No. 14895210.4", The Hague, dated Apr. 6, 2018.

\* cited by examiner

MOBILE TERMINAL

CROSS-REFERENCE TO RELATED APPLICATIONS

This application is a continuation of International Patent Application No. PCT/CN2014/088291, with an international filing date of Oct. 10, 2014, designating the United States, which is based on Chinese Patent Application No. 2014102685893, filed Jun. 16, 2014. The contents of these specifications are incorporated herein by reference.

BACKGROUND OF THE INVENTION

Field of the Invention

The present invention relates to the technical field of mobile terminals, and in particular, to a mobile terminal with a touch screen equipped with a sensing identification module.

Description of the Related Art

At present, a press-type capacitive sensing identification module of the latest generation of smart handheld devices at home and abroad is embedded into a slot opened on a touch screen such that the sensing identification module is exposed to a user's fingers for touches. Such design not only increases manufacturing difficulty of the touch screen, but also enhances sense of difference which is brought by the independently assembled sensing identification module from the visual and tactile perspectives. This affects the entire structure, appearance and user experience of the device.

SUMMARY OF THE INVENTION

The present invention is intended to solve at least one of the above problems in the related art.

To this end, one objective of the present invention is to provide a mobile terminal, where a sensing identification module is integrated into a touch screen thereof. With this technical solution, the problem of sense of difference which is brought by the independently assembled sensing identification module is solved from the visual and tactile perspectives, the manufacturing procedure is simplified, production and utilization efficiencies are improved, and user's satisfaction of is bettered.

The present invention is implemented by: a mobile terminal, including a touch screen, the touch screen including a touch cover plate. The touch screen further includes a sensing identification module, the touch cover plate covers the sensing identification module.

To be specific, the touch cover plate includes a first part and a second part, a thickness of the second part being less than a thickness of the first part, the second part entirely or partially covers the sensing identification module.

In one embodiment, an upper surface of the touch cover plate is partially recessed downwardly to form the second part of the touch cover plate.

In another embodiment, a lower surface of the touch cover plate is partially recessed upwardly to form the second part of the touch cover plate, the sensing identification module is entirely or partially located inside the second part.

Further, the touch screen further comprises a touch sensor, the touch sensor is located beneath the touch cover plate.

In one embodiment, a through hole is arranged between an upper surface and a lower surface of the touch sensor, the sensing identification module is placed in the through hole.

Further, the touch screen further includes a reinforcing layer, the reinforcing layer is located beneath the touch cover plate.

In one embodiment, a through hole is arranged between an upper surface and a lower surface of the reinforcing layer, the sensing identification module is placed in the through hole.

Further, a lower surface of the touch cover plate is further provided with a silk screen layer.

Preferably, the sensing identification module includes at least one of a fingerprint identification module, a heartbeat identification module and a blood oxygen identification module.

The additional aspects and advantages of the present invention are partially illustrated in the following description, and the other portions would become more obvious from the following description or would be known from the practice of the present invention.

DETAILED DESCRIPTION OF THE EMBODIMENTS

Figure 1:
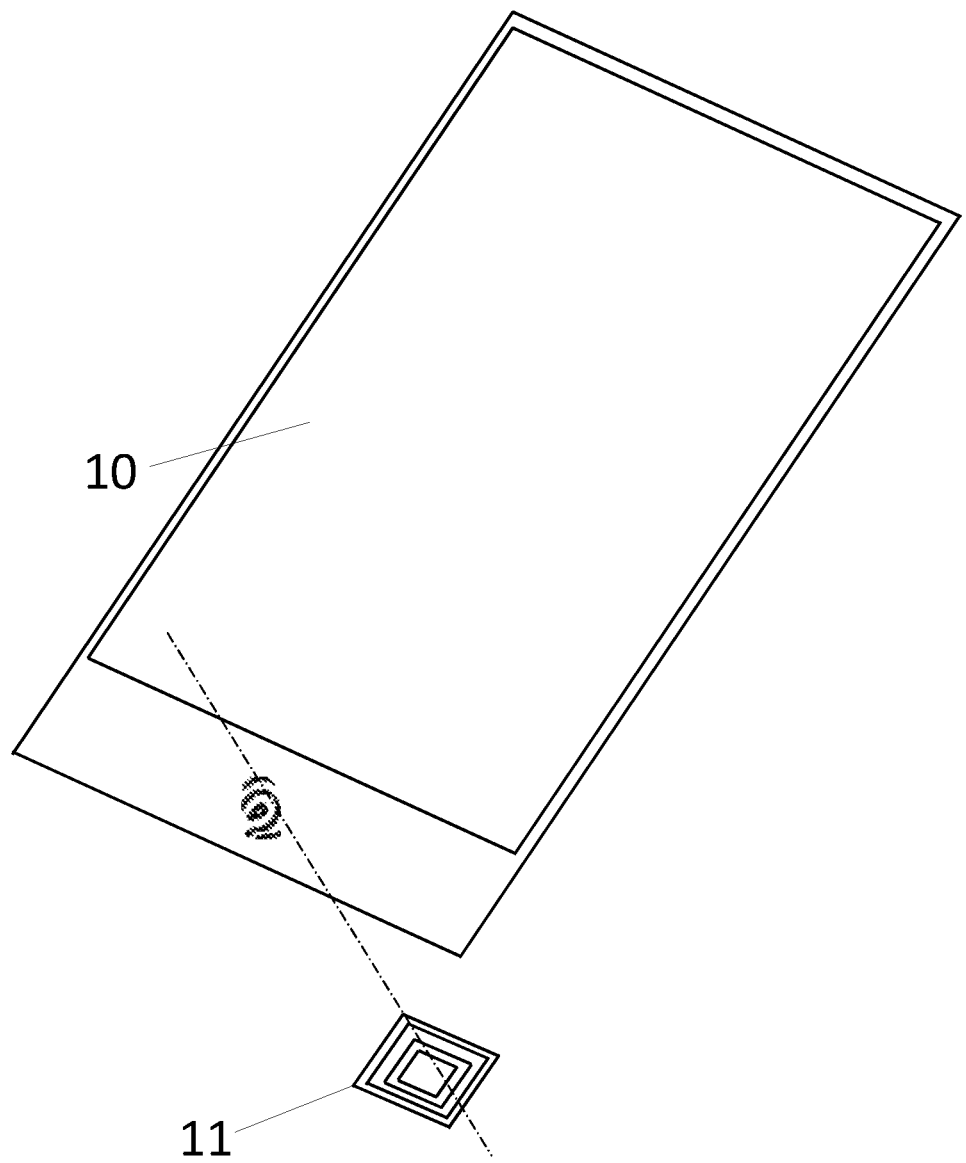
FIG. 1 is a schematic three-dimensional exploded view of a mobile terminal according to an embodiment of the present invention.

The embodiments of the present invention are described in detail hereinafter. Examples of the described embodiments are given in the accompanying drawings, wherein the identical or similar reference numerals constantly denote the identical or similar elements or elements having the identical or similar functions. The specific embodiments described with reference to the attached drawings are all exemplary, and are intended to illustrate and interpret the present invention, which shall not be construed as causing limitations to the present invention.

In the description of the present invention, it should be understood that the terms "thickness", "upper", "lower", "front", "rear", "left", "right", "vertical", "horizontal", "top", "bottom", "inner", "outer" and the like indicate orientations and position relationships which are based on the illustrations in the accompanying drawings, and these terms are merely for ease and brevity of the description, instead of indicating or implying that the devices or elements shall have a particular orientation and shall be structured and operated based on the particular orientation. Accordingly, these terms shall not be construed as limiting the present invention.

In the description of the present invention, it should be noted that unless otherwise specified and defined, the terms "mounted", "coupled", "connected" and "fixed" and derivative forms thereof shall be understood in a broad sense, which, for example, may be understood as fixed connection, detachable connection or integral connection; may be understood as mechanical connection or electrical connection, or understood as direct connection, indirect connection via an intermediate medium, or communication between the interiors of two elements or interactions between two elements. Persons of ordinary skill in the art may understand the specific meanings of the above terms in the present invention according to the actual circumstances and contexts.

Figure 2:
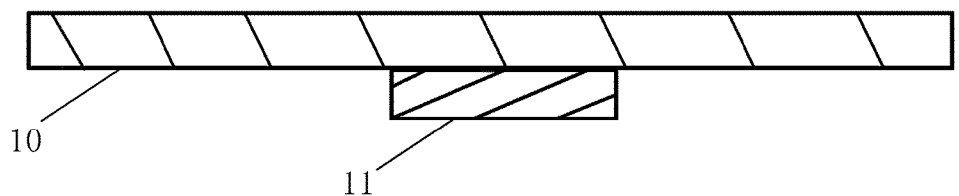
FIG. 2 is a schematic section view of the mobile terminal as illustrated in FIG. 1.

As illustrated in FIG. 1 and FIG. 2, this embodiment discloses a mobile terminal, including a touch screen. The touch screen includes a touch cover plate 10 and a sensing identification module 11. The touch cover plate 10 covers the sensing identification module 11. Preferably, the sensing identification module 11 is one or more of a fingerprint identification module, a heartbeat identification module and a blood oxygen identification module.

In this embodiment, the touch cover plate 10 includes a first part 101 and a second part 102, a thickness of the second part 102 is less than a thickness of the first part 101, and the second part 102 entirely or partially covers the sensing identification module 11. Objectives of such design are to reduce the thickness of the touch cover plate 10 in a region where the sensing identification module 11 is located, enhance signal strength, and facilitate the sensing identification module 11 in data acquisition. Moreover, such design can also indicate the location where the sensing identification module 11 is located, and give convenience to user's operations.

Figure 3:
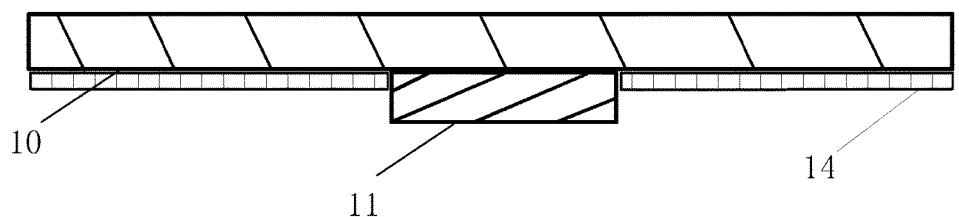
FIG. 3 is another schematic section view of the mobile terminal as illustrated in FIG. 1.

As illustrated in FIG. 3, a lower surface of the touch cover plate 10 is further provided with a reinforcing layer 14. In one embodiment, a through hole is arranged between an upper surface and a lower surface of the reinforcing layer 14, and the sensing identification module 11 is placed in the through hole.

The lower surface of the touch cover plate 10 is further provided with a silk screen layer (not labeled with reference numeral), and the silk screen layer is configured to indicate the location where the sensing identification module 11 is located, and give convenience to user's operations.

Several embodiments of the touch cover plate are specifically described hereinafter.

Embodiment 1

Figure 4:
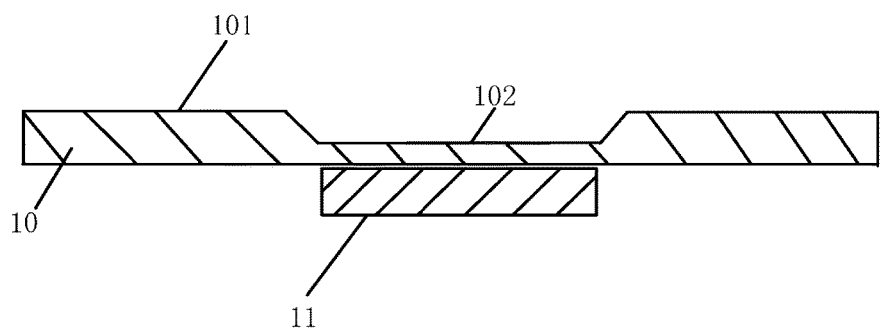
FIG. 4 is still another schematic section view of the mobile terminal as illustrated in FIG. 1.
Figure 5:
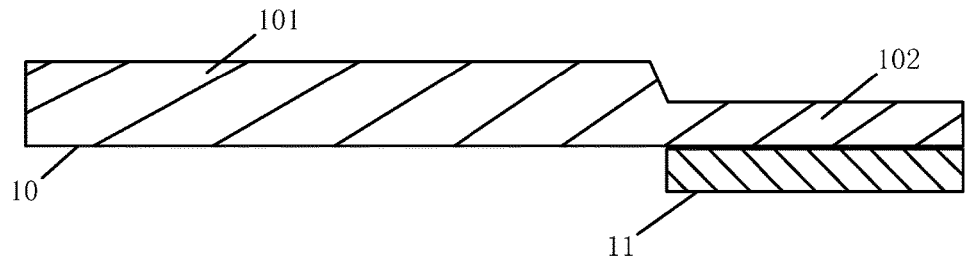
FIG. 5 is yet still another schematic section view of the mobile terminal as illustrated in FIG. 1.

As illustrated in FIG. 4 and FIG. 5, an upper surface of the touch cover plate 10 is partially recessed downwardly to form the second part 102 of the touch cover plate 10. The rest part of the touch cover plate 10, except the recess part, is the first part 101, and the sensing identification module 11 is located beneath the second part 102. This reduces the thickness of the touch cover plate in a region where the sensing identification module is located, enhances signal strength, and facilitates the sensing identification module 11 in data acquisition.

Embodiment 2

Figure 6:
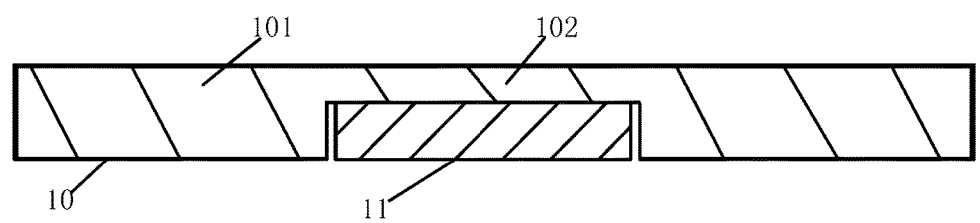
FIG. 6 is yet still another schematic section view of the mobile terminal as illustrated in FIG. 1.
Figure 7:
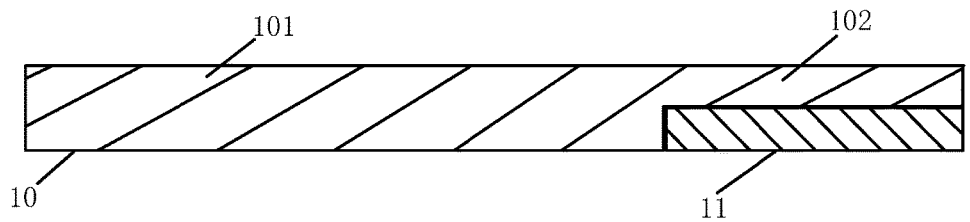
FIG. 7 is yet still another schematic section view of the mobile terminal as illustrated in FIG. 1.

As illustrated in FIG. 6 and FIG. 7, a lower surface of the touch cover plate 10 may be partially recessed upwardly to form the second part 102 of the touch cover plate 10. The rest part of the touch cover plate 10, except the recess part, is the first part 101, and the sensing identification module 11 is partially or entirely received inside the second part 102.

Figure 8:
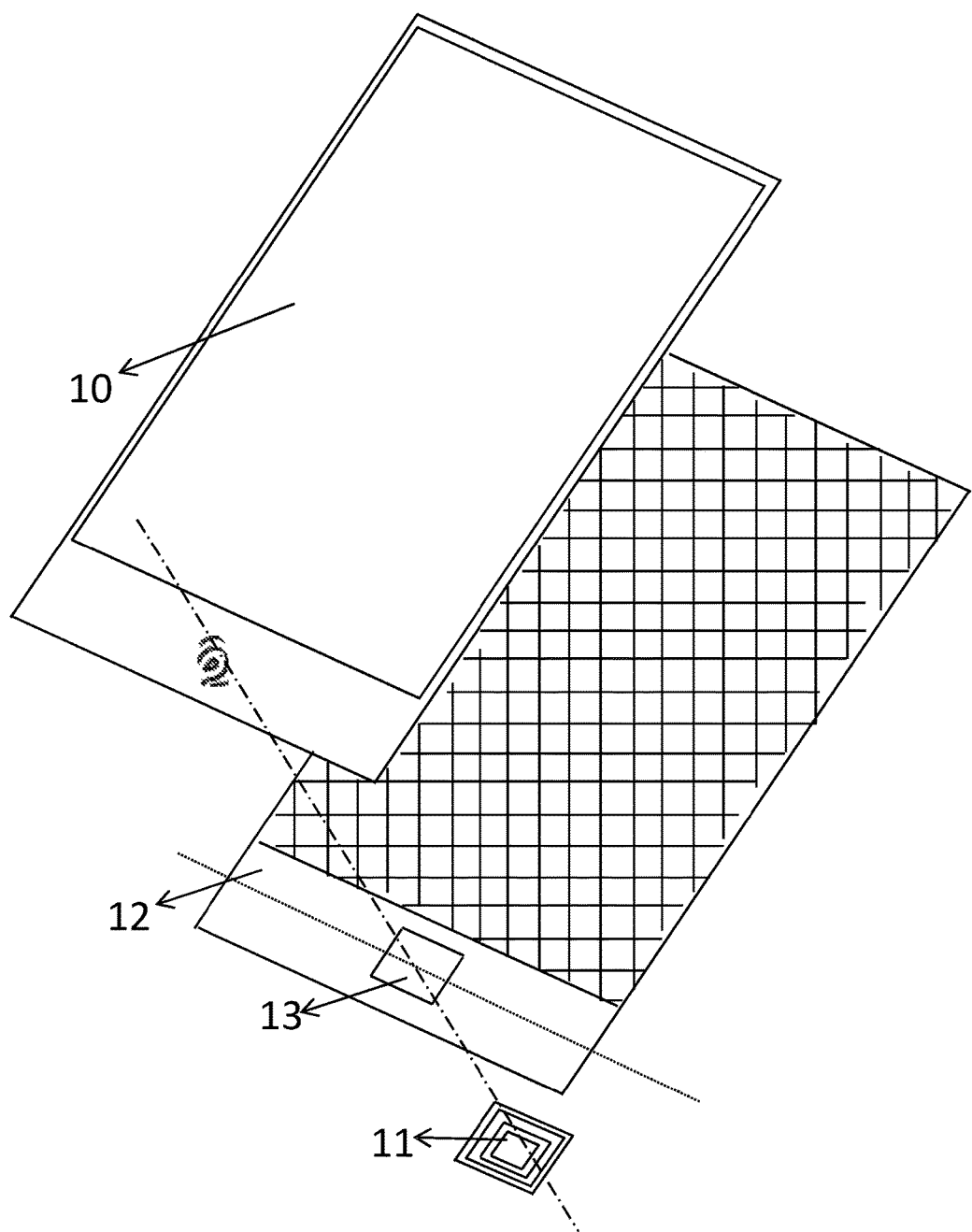
FIG. 8 is another schematic three-dimensional exploded view of the mobile terminal according to an embodiment of the present invention.
Figure 9:
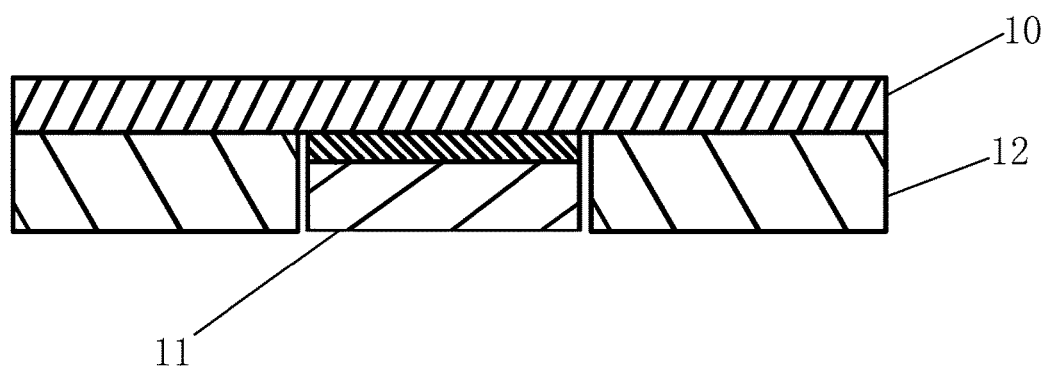
FIG. 9 is a schematic section view of the mobile terminal as illustrated in FIG. 7.

As illustrated in FIG. 8 and FIG. 9, the touch screen further comprises a touch sensor 12, where the touch sensor 12 is located beneath the touch cover plate 10. Preferably, a through hole 13 may be arranged between an upper surface and a lower surface of the touch sensor 12, and the sensing identification module 11 is placed in the through hole. Nevertheless, the sensor 12 may alternatively be placed in a side-by-side manner with the sensing identification module 11, and beneath the touch cover plate 10.

It should be noted that all control circuits, sensing circuits, memory circuits, and filters and boost circuits may be integrated in the sensing identification module 11. The location of the sensing identification module 11 is not specifically limited. For example, the sensing identification module 11 may be arranged at the location of a control board close to a physical HOME key or a virtual HOME key.

The touch cover plate 10 may be made from material with a high dielectric constant, high hardness and high durability, for example, the touch cover plate 10 may be made form a tempered glass sheet or a sapphire glass sheet.

In the embodiments of the present invention, the sensing identification module 11 is integrated into a touch screen assembly, and a full touch panel is used. In this way, the problem of sense of difference which is brought by the independently assembled sensing identification module 11 is solved from the visual and tactile perspectives, the manufacturing procedure is simplified, production and utilization efficiencies are improved, and user's satisfaction is enhanced.

In addition, it should be noted that the thickness of the touch cover plate 10 depends on material properties, for the reason that the touch performance of the sensor 12 is affected if the touch cover plate 10 is too thin.

When the sensing identification module is a fingerprint identification module, the fingerprint identification module includes a series of complicated circuits, including: a fingerprint identification sensor circuit, a control circuit, a memory circuit, a filter circuit, and the like, which are devices capable of implement fingerprint image acquisition. The fingerprint identification sensor circuit is formed by a series of analog circuit matrixes having a signal acquisition function. The fingerprint identification module is internally provided with a dust-proof cushion, which is configured to fix the fingerprint identification module, isolate dust, sweat, water and the like from entering the interior of the fingerprint identification module.

The fingerprint identification module uses the multi-chip package technology, and interconnection is achieved through a circuit substrate. The fingerprint identification sensor circuit is arranged on the front side of the entire fingerprint identification module, and the control circuit and the like on the rear side thereof are all protected by a filled plastic encapsulation body. The plastic encapsulation body may be provided in a complete mold process, or may be formed through the drop glue protection technique. During the process of the plastic encapsulation, epoxy resins (compound) or other materials similar to high temperature resistance and scratch resistance materials may be used. Nevertheless, the process of the plastic encapsulation is not limited herein, as long as the circuits are protected from damages.

It should be noted that the mobile terminal herein may be a mobile phone, a tablet computer, or any device having a touch function.

In the description of the present specification, reference terms such as "an embodiment", "some embodiments", "examples", "specific examples", "some examples", or the like are intended to refer to that the specific features, structures, materials, or characteristics which are described in combination with the embodiments or examples are comprised in at least one embodiment or example of the present invention. In this specification, schematic expressions of the above terms do not necessarily indicate the same embodiments or examples. In addition, the described specific features, structures, materials, or characteristics may be combined in any one or multiple embodiments or examples in a suitable way. In addition, in case of no contradiction, a person skilled in the art may incorporate or combine different embodiments or examples and features of different embodiments or examples described in this specification.

Although the above description illustrates the embodiments of the present invention, it can be understood that the embodiments are merely exemplary, and shall not be construed as limitations to the present invention. Persons of ordinary skill in the art may derive variations, modifications, and replacements to the above embodiments within the scope of the present invention.

INDUSTRIAL PRACTICABILITY

According to embodiments of the present invention, the touch cover plate and the induction identification module are integrated on the touch screen, a full touch panel is adopted, the problem of the sense of difference caused by independent assembly of the induction identification module in vision and touch is solved, the processing procedure is reduced, the efficiency of production and utilization is improved, and the satisfaction degree of users is improved.

What is claimed is:

1. A mobile terminal, comprising:
a touch screen, the touch screen comprising a touch cover plate,
wherein the touch screen further comprises a sensing identification module, the touch cover plate covers the sensing identification module;
wherein the touch sensor is placed in a side-by-side manner with the sensing identification module, and beneath the touch cover plate;
wherein the touch cover plate comprises a first part and a second part, a thickness of the second part is less than that of the first part, and the second part entirely or partially covers the sensing identification module; and
wherein the sensing identification module comprises at least one of a fingerprint identification module, a heartbeat identification module and a blood oxygen identification module.

2. The mobile terminal according to claim 1, wherein the sensing identification module further comprises at least one of a heartbeat identification module and a blood oxygen identification module.

3. The mobile terminal according to claim 1, wherein an upper surface of the touch cover plate is partially recessed downwardly to form the second part, a rest part of the touch cover plate except the recess part is the first part, and the sensing identification module is located beneath the second part.

4. The mobile terminal according to claim 1, a lower surface of the touch cover plate is partially recessed upwardly to form the second part, a rest part of the touch cover plate except the recess part is the first part, and the sensing identification module is partially or entirely received inside the second part.

5. The mobile terminal according to claim 1, wherein a lower surface of the touch cover plate is further provided with a silk screen layer.

6. The mobile terminal according to claim 1, wherein the touch screen further comprises a reinforcing layer, the reinforcing layer is located beneath the touch cover plate.

7. The mobile terminal according to claim 6, wherein a through hole is arranged between an upper surface and a lower surface of the reinforcing layer, the sensing identification module is placed in the through hole.

8. An apparatus, comprising:
a touch cover plate;
a touch sensor; and
a sensing identification module arranged beneath the cover plate;
wherein the touch sensor is placed in a side-by-side manner with the sensing identification module, and beneath the touch cover plate;
wherein the touch cover plate comprises a first part and a second part having a thickness less than the first part, and the second part entirely or partially covers the sensing identification module; and
wherein the sensing identification module comprises at least one of a fingerprint identification module, a heartbeat identification module and a blood oxygen identification module.

9. The apparatus according to claim 8, wherein the fingerprint identification module comprises a fingerprint identification sensor circuit with a series of analog circuit matrixes for providing a signal acquisition function, and a dust-proof cushion is provided in the fingerprint identification module for fixing the fingerprint identification module and isolating undesired object from entering an interior of the fingerprint identification module.

10. The apparatus according to claim 8, wherein an upper surface of the touch cover plate is partially recessed downwardly to form the second part, a rest part of the touch cover plate except the recess part is the first part, and the sensing identification module is located beneath the second part.

11. The apparatus according to claim 8, a lower surface of the touch cover plate is partially recessed upwardly to form the second part, a rest part of the touch cover plate except the recess part is the first part, and the sensing identification module is partially or entirely received inside the second part.

12. The apparatus according to claim 8, wherein a lower surface of the touch cover plate is further provided with a silk screen layer.

13. The apparatus according to claim 8, wherein the touch screen further comprises a reinforcing layer, the reinforcing layer is located beneath the touch cover plate.

14. The apparatus according to claim 13, wherein a through hole is arranged between an upper surface and a lower surface of the reinforcing layer, the sensing identification module is placed in the through hole.

* * * * *